(12) United States Patent
Lejeune et al.

(10) Patent No.: US 6,861,252 B2
(45) Date of Patent: Mar. 1, 2005

(54) SENSORS FOR THE DETECTION OF AN ANALYTE

(75) Inventors: Keith E. Lejeune, Pittsburgh, PA (US); Markus Erbeldinger, Pittsburgh, PA (US)

(73) Assignee: Agentase, LLC, Pittsburgh, PA (US)

( * ) Notice: Subject to any disclaimer, the term of this patent is extended or adjusted under 35 U.S.C. 154(b) by 185 days.

(21) Appl. No.: 10/269,487

(22) Filed: Oct. 11, 2002

(65) Prior Publication Data

US 2004/0023369 A1 Feb. 5, 2004

Related U.S. Application Data

(60) Provisional application No. 60/328,524, filed on Oct. 11, 2001.

(51) Int. Cl.[7] ............................................. C12M 1/34
(52) U.S. Cl. ............................ 435/288.2; 435/287.6; 435/309.1; 422/58; 422/102; 422/103
(58) Field of Search ................................. 422/102, 103

(56) References Cited

U.S. PATENT DOCUMENTS 4,562,043 A * 12/1985 Mennen et al. ............... 422/56
4,978,504 A * 12/1990 Nason ............................. 422/61
6,291,200 B1 * 9/2001 LeJeune et al. ............... 435/20
2002/0150959 A1 * 10/2002 Lejeune et al. ............... 435/18
2002/0182662 A1 * 12/2002 Lejeune et al. ............... 435/18

* cited by examiner

*Primary Examiner*—William H. Belsner
(74) *Attorney, Agent, or Firm*—Craig G. Cochenour; Buchanan Ingersoll PC

(57) ABSTRACT

A sensor for the detection of an analyte includes a first reagent in one section of the housing and at least a second reagent in another section of the housing. The sensor also includes a reservoir of a carrier fluid (that is, a liquid or a gas) within the housing. A release mechanism of the sensor is in operable connection with the reservoir so that when the release mechanism is activated, the carrier fluid is released from the reservoir. The carrier fluid mobilizes the second reagent to contact the first reagent with the second reagent. The interaction of the first reagent and the second reagent is affected by the presence or absence of the analyte to cause a measurable change of state within the sensor.

36 Claims, 4 Drawing Sheets

SENSORS FOR THE DETECTION OF AN ANALYTE

CROSS-REFERENCE TO RELATED APPLICATION

This application claims benefit of U.S. Provisional Patent Application Ser. No. 60/328,524, filed Oct. 11, 2001, the disclosure of which is incorporated herein by reference.

The invention described herein was made in the course of work supported in part by the United States of America, Department of Defense, Contract No. DAMD17-99-C-9016. The Government may have certain rights in this invention.

BACKGROUND OF THE INVENTION

The present invention relates to sensors for the detection of an analyte and, particularly, to sensors for the detection of hazardous or toxic analytes.

References set forth herein may facilitate understanding of the present invention or the background of the present invention. Inclusion of a reference herein, however, is not intended to and does not constitute an admission that the reference is available as prior art with respect to the present invention.

There are many types of sensors designed to detect the presence of chemical species, for example, on surfaces or within solutions. Such sensors exhibit signals based on a wide variety of chemical, electrical, or physical responses. Many such sensors are based upon "negative responses". In negative response sensors, the chemical analyte of interest inhibits or retards a chemical or physical process that would otherwise take place within the sensor in the analyte's absence. The term "negative response sensor" thus generally refers to sensors in which the presence of a target analyte results in the absence of or the reduction of a signal change or a signal change.

Enzymatic proteins are remarkable natural catalysts in that they selectively catalyze many reactions under relatively mild reaction conditions. Enzymes also offer the potential to perform sterio- and regio-selective reactions not readily accomplished with conventional chemistry. As used herein, the term "enzyme" refers generally to proteins that catalyze biochemical reactions. These "biopolymers" include amide-linked amino acids and typically have molecular weights of 5,000 or greater. A compound for which a particular enzyme catalyzes a reaction is typically referred to as a "substrate" of the enzyme.

In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases.

Enzymes have been known since the early 1960's to be useful tools for detecting the presence of chemical species. Rogers, K. R., Biosensors Bioelectronics, 10, 533 (1995). A number of enzymatic biosensors have been designed to detect a variety of different compounds including, for example, glucose, creatinine, urea, and cholinesterase inhibitors. Parente, A. H., Marques, E. T. Jr., *Appl. Biochem. Biotechnol.* 37, 3, 267 (1992); Yang, S., Atanasov, P., Wilkins, E., *Ann. Biomed. Eng.*, 23, 6, 833 (1995). U.S. Pat. No. 5,858,186 describes a urea-based biosensor in which substrate hydrolysis is monitored with a pH electrode. U.S. Pat. Nos. 5,945,343 and 5,958,786 describe enzyme-based polymer sensors which fluoresce in the presence of ammonia, which is enzymatically produced from urea and creatinine respectively. In addition U.S. Pat. No. 4,324,858 describes the utilization of cholinesterase for the colorimetric detection of organophosphorus pesticides and nerve agents. A related patent, U.S. Pat. No. 4,525,704 describes the use of cholinesterases and electrical currents in detecting toxic gases.

Generally, enzymatic biosensors function by one of two methods: (1) the sensing enzyme converts an otherwise undetectable compound into another or series of compounds which can be detected by visual, chemical, or electrical techniques; or (2) the enzyme is inhibited by the presence of the compound of interest and enzyme inhibition is linked to a measurable quantity.

Independent of the method of use, the signals of enzyme-based biosensors are often limited in practical application by the nature of enzyme activity. Like non-enzymatic sensors, most enzymatic sensors are negative response sensors. For example, in many enzymatic sensors the sensor provides a positive response in the presence of target analyte only in the case that the target analyte is a substrate for the enzyme of the sensor. In other words a noticeable change in the sensor indicates the presence of a target analyte. If the detection of enzyme inhibitors or the detection of substrate deficiency is desired, existing approaches rely on negative response signals, or the absence or reduction of an enzymatic reaction, to indicate the presence of inhibitors or the absence of target compounds.

U.S. patent application Ser. No. 09/858,686, filed May 7, 2001 and entitled Positive Response Biosesensors and Other Sensors, assigned to the assignee of the present invention, the disclosure of which is incorporated herein by reference, discloses sensors and methods in which the non-intuitive nature of a previously negative response sensors are changed to a more intuitive, positive response system. The methods and devices of U.S. patent application Ser. No. 09/858,686 are, for example, well suited for application in enzymatic biosensors and enzymatic biosensing methods.

It is very desirable to further develop sensors and sensing method through which the non-intuitive nature of negative response enzymatic and other sensors can be changed to a more intuitive positive response system.

SUMMARY OF THE INVENTION

In one aspect, the present invention provides a sensor for the detection of an analyte including a first reagent in one section of the housing and at least a second reagent in another section of the housing. The sensor also includes a reservoir of a carrier fluid (that is, a liquid or a gas) within the housing. A release mechanism of the sensor is in operable connection with the reservoir so that when the release mechanism is activated, the carrier fluid is released from the reservoir. The carrier fluid mobilizes the second reagent to contact the first reagent with the second reagent. The interaction of the first reagent and the second reagent is affected by the presence or absence of the analyte to cause a measurable change of state within the sensor.

In one embodiment, the second reagent is in the carrier fluid prior to activation of the release mechanism. In another embodiment, the second reagent is the carrier fluid.

The sensor can also include a third reagent in one section of the housing and at least a fourth reagent in another section of the housing. In this embodiment, the carrier fluid mobilizes the third reagent to contact the third reagent with the fourth reagent. The interaction of the third reagent and the fourth reagent is affected by the presence or absence of the analyte to cause a second measurable change of state within the sensor, which can be different from the measurable change of state caused by the interaction of the first reagent and the second reagent.

The second reagent can be immobilized in a first polymer medium. Likewise, the fourth reagent can be immobilized in the first polymer medium. The first reagent and the third reagent can be incorporated within a second polymer medium. In one embodiment, the activator releases the carrier fluid when the first polymer medium is contacted with a surface to be tested for presence of the analyte.

The sensor can further include a removable transparent housing member to enclose the sensor. The sensor can also include a barrier to prevent contact between the first polymer medium and the second polymer medium.

In another aspect, the present invention provides a sensor for detecting an analyte in an environment including a first reaction system including a first enzyme and a substrate for the first enzyme. The analyte inhibits the first enzyme. The sensor further includes at least a second reaction system including at least a first reagent and a second reagent that interact to produce a first detectable state when the first enzyme is inhibited. The first enzyme and the substrate are separated within the sensor. The first reagent and the second reagent are also separated within the sensor. The sensor also includes a reservoir containing a carrier fluid and an activator to release the carrier when the sensor it brought into contact with an environment to be tested for presence of the analyte. The carrier mobilizes the substrate for the first enzyme to contact the first enzyme and mobilizes the first reagent to contact the second reagent.

The reaction of the first reaction system can, for example, produce a second detectible state, different from the first detectible state. In one embodiment, the reaction of the first reaction system causes pH to change in a first direction and the reaction of the second reaction system causes pH to change in a second direction, opposite of the first direction.

The first enzyme can, for example, be a hydrolase. In one embodiment, the first enzyme is a cholinesterase. The analyte can, for example, be a nerve agent.

The second reaction system can also include a second enzyme and a substrate for the second enzyme. In one embodiment, the first enzyme is a hydrolase and the second enzyme is a different hydrolase.

The first detectible state can, for example, be a colorimetric change. The reaction of the first reaction system can produce a second detectible state, different from the first detectible state. The reaction of the first reaction system can, for example, cause a first colorimetric change and the reaction of the second reaction system can cause a second calorimetric change, which is different from the first colorimetric change. In one embodiment, the first detectible state arises from the presence of a first pH sensitive dye producing a calorimetric change and the second detectible state is a colorimetric change different from the calorimetric change of the first detectible state.

The first enzyme can, for example, be immobilized in a polymer medium. In one embodiment, the first enzyme is immobilized in a first polymer medium, and the second reagent is a second enzyme that is also immobilized in the first polymer medium. The substrate for the first enzyme can be incorporated within a second polymer medium, and the first reagent (a substrate for the second enzyme) is also incorporated within the second polymer medium.

The activator can, for example, release the carrier fluid when the first polymer medium is contacted with a surface to be tested for presence of the analyte. The sensor can include a removable transparent housing member to enclose the sensor. The sensor can also include a barrier to prevent contact between the first polymer medium and the second polymer medium.

DETAILED DESCRIPTION OF ONE EMBODIMENT OF THE INVENTION

Figure 1:
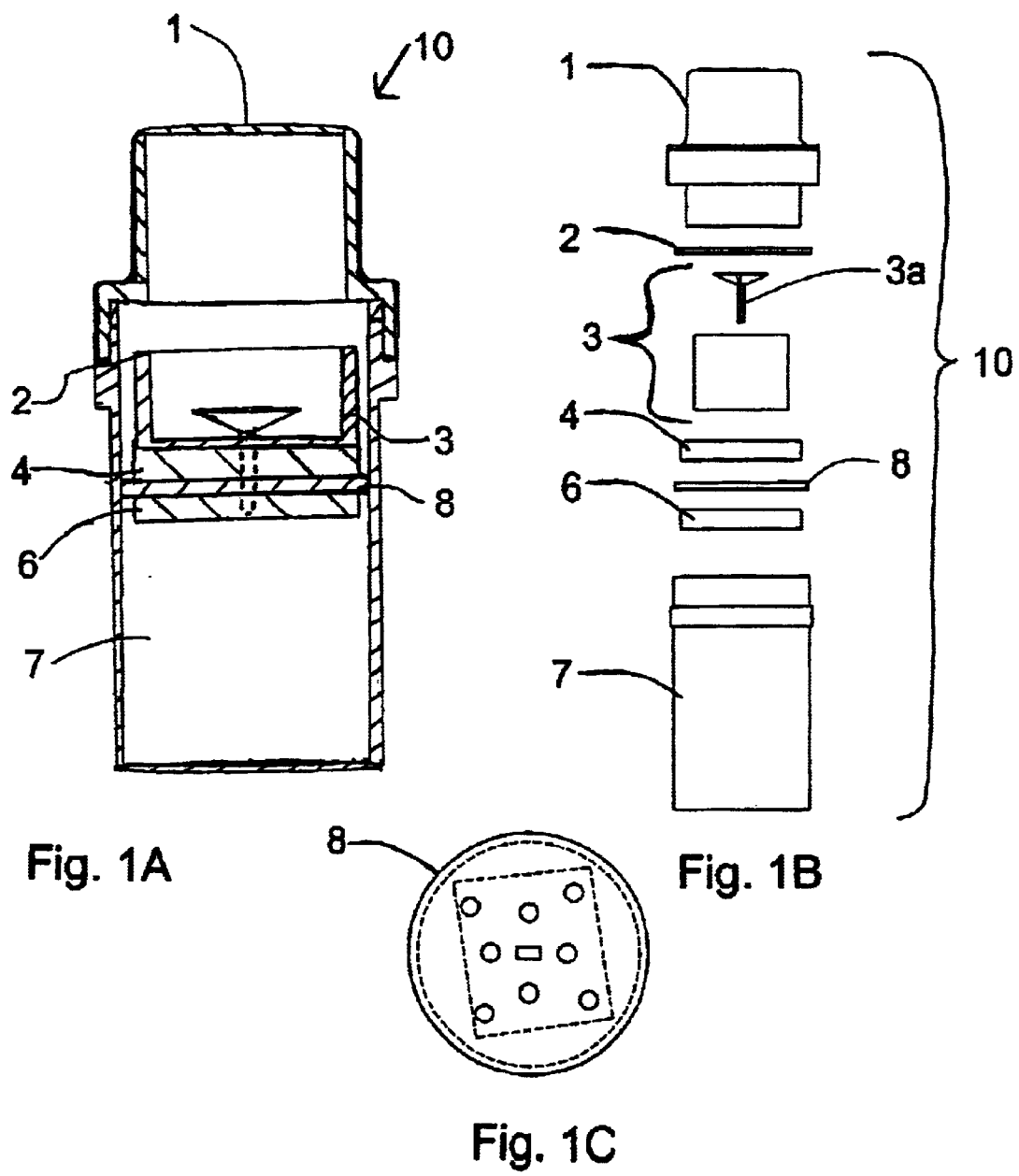
FIG. 1A illustrates a side, cross-sectional view of one embodiment of a sensor of the present invention in a closed state.
FIG. 1B illustrates a side view of the sensor of FIG. 1A in a disassembled or exploded state.
FIG. 1C illustrates a top plan view of barrier 8 of the sensor of the present invention.

In one embodiment, the present invention provides sensors that can, for example, be hand held devices including two formulated polymers within an engineered applicator device. FIGS. 1A and 1B illustrate the design of one embodiment of a sensor 10 and the nature of its components.

Sensor 10 includes a reservoir or container 1 that carries a fluid (that is, a gas or a liquid) carrier or vehicle (for example, water) that can be released to initiate one or more reactions. In general, the carrier fluid mobilizes one or more reagents to contact other reagents within sensor 10 and initiate one or more reactions. As used herein, the term "reagent" refers to a component that interacts with other components in a reaction (for example, a reactant or a catalyst). In the embodiment of FIGS. 1A and 1B, reservoir 1 is formed as part of an upper housing portion of sensor 10. Reservoir 1 cooperates with a lower housing portion 7 (via, for example, threading) to enclose the components of sensor 10.

In one embodiment, the reaction scheme of sensor 10 was an enzymatic equilibrium reaction scheme in which a water carrier or vehicle provided both required moisture and enzyme substrate mobility by washing/mobilizing substrates from a substrate-containing polymer disk 4 to an enzyme-containing polymer disk 6. For example, in a sensor for the detection of a toxic organophosphate, substrate-containing polymer disk 4 was a polyurethane disk with butyrylcholine, urea and indoxyl acetate substrates, all of which diffused out of substrate-containing polymer disk 6 when a release valve 3 (or other release mechanism) was engaged to release carrier water contained in reservoir 1. A washer 2 provided a seal between reservoir 1 and release valve 3. In one embodiment, a spring-loaded release valve available in an applicator available from Waldwick Plastics of Waldwick, N.J. (20 mm release valve) was used in sensor 10. Release valve 3 or other release mechanism (for example, an openable membrane) ensures that the carrier water (or other fluid carrier) remains within reservoir 1 until released on demand by firmly pressing enzyme-containing polymer disk 6 (and thereby a release pin 3a of release valve 3) against a surface.

Enzyme-containing polymer disk 6 of sensor 10 was a polyurethane disk with covalently polymerized butylcholinesterase (BChE) and urease enzymes incorporated therein. These enzymes can be polymerized within a polymer disk/matrix as described in U.S. Pat. No. 6,291,200, assigned to the assignee of the present invention, the disclosure of which is incorporated herein by reference. U.S. Pat. No. 6,406,876, the disclosure of which is incorporated herein by reference, also described the incorporation of enzymes into polymer media. Enzyme-containing polymer disk 6 also included a pH-sensitive indicator which can, for example, be physically entrapped within the polymer or covalently linked thereto. The sensor further included a barrier 8 (for example, a porous nylon separation disk) to prevent enzyme-containing polymer 6 from being in direct contact with substrate-containing polymer(s). Such direct contact is undesirable in that it can result in reaction prior to operator activation of the sensor 10.

As described above, sensor 10 preferably further includes lower containment vessel or housing portion 7 to protect the internal components of sensor 10 and to contain any hazardous contamination. Preferably, at least a portion of housing 7 is transparent or translucent to observe state changes (for example, color changes) that occur upon activation of sensor 10.

Figure 2:
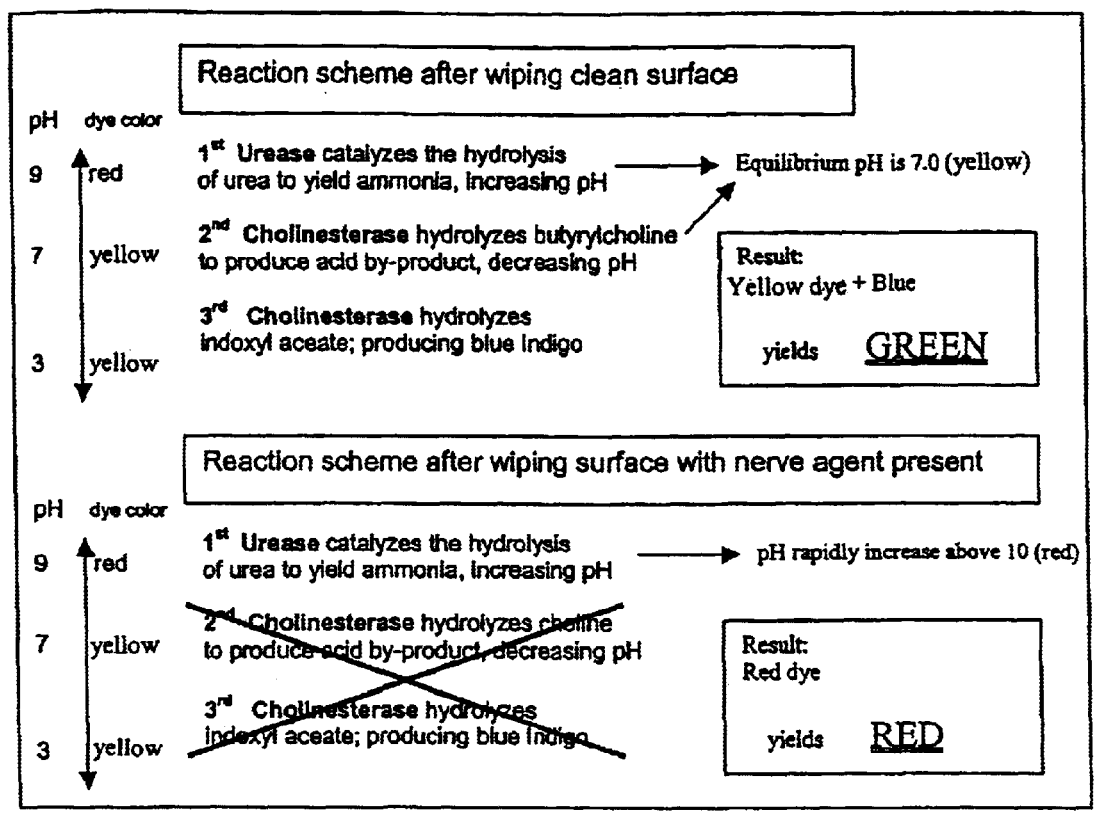
FIG. 2 illustrates a reaction scheme of one embodiment of a sensor of the present invention.

Sensor 10 is supplied in a closed state in which reservoir cap 1 and lower housing portion 7 are connected as illustrated in FIG. 1A. During use, lower housing portion 7 is removed and enzyme-containing polymer disk 6 is pressed or wiped against a surface to be tested for the presence of the analyte. As described above, pressing enzyme-containing polymer disk 6 against the surface activates release valve 3 to release water from reservoir 1. The water released from reservoir 1 mobilized the substrates(s) within substrate-containing polymer disk 4 so that such substrates come into contact with the enzymes of enzyme-containing polymer disk 6. The presence or absence of the analyte on the surface affects the nature of a reaction occurring in sensor 10, which is translated into an observable state change within sensor 10, as described for example in FIG. 2. After exposure of enzyme-containing polymer disk 6 to a surface potentially contaminated with a toxic analyte, lower housing portion 7 is preferably reconnected to reservoir cap 1 to contain contamination and reduce the likelihood of injury to the user of sensor 10. Signal development can subsequently be viewed through the transparent housing portion 7.

In that regard, the co-immobilized pH sensitive indicator of enzyme-containing polymer disk 6 transitions from yellow to red as the pH increases from 7 to 9. Hydrolysis of the additional cholinesterase substrate, indoxyl acetate, of substrate-containing polymer disk 4 results in the production of blue indigo, providing sensor 10 with a mode of verifying performance and better signal differentiation. A description of the reaction scheme and signal response of sensor 10 is provided in FIG. 2. Such reaction schemes are described in U.S. patent application Ser. No. 09/858,686, filed May 7, 2001 and entitled Positive Response Biosesensors and Other Sensors, assigned to the assignee of the present invention, the disclosure of which is incorporated herein by reference.

Figure 3:
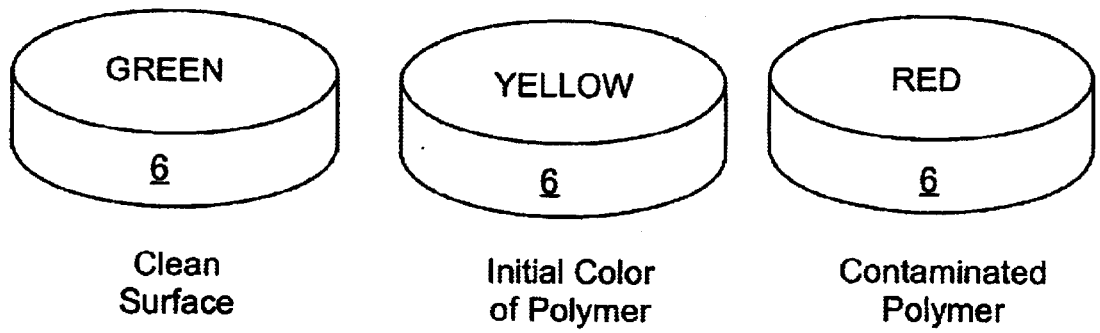
FIG. 3 illustrates signal development in one embodiment of a sensor of the present invention in which an initially yellow polymer disk turns green in the absence of an analyte and turns red in the presence of an analyte.

FIG. 3 illustrates the straightforward-to-read signal exhibited by sensor 10. Similar to a traffic light, the originally yellow enzyme containing polymer disk 6 of sensor 10 develops a red color after exposure to a contaminated surface and develops a green color to indicate a clean surface. In one example of sensor 10, red color was developed in less than 2 minutes, while the full green color development exhibited in FIG. 2 required approximately 20 minutes.

Figure 4:
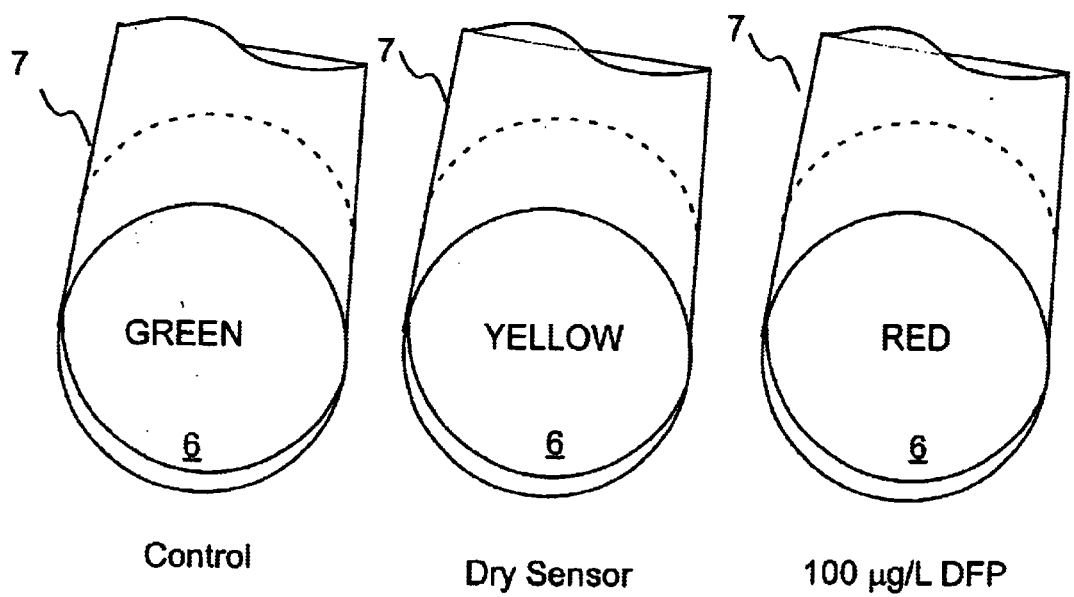
FIG. 4 illustrates several sensors of the present invention exposed to no or minute quantities of diisopropyl fluorophosphate (DFP) analyte, showing sensitivity toward cholinesterase inhibitors.

FIG. 4 illustrates that the detection limit of several tested examples of sensor 10 when using these protocols on diisopropyl fluorophosphate (DFP) was less than 100 parts per billion (ppb). Detection limits can vary for different agents in the case of sensor 10 as a function of their ability to inhibit cholinesterase. Highly toxic materials such as warfare grade agents will be detected at even lower concentration levels than observed with DFP.

Figure 5A:
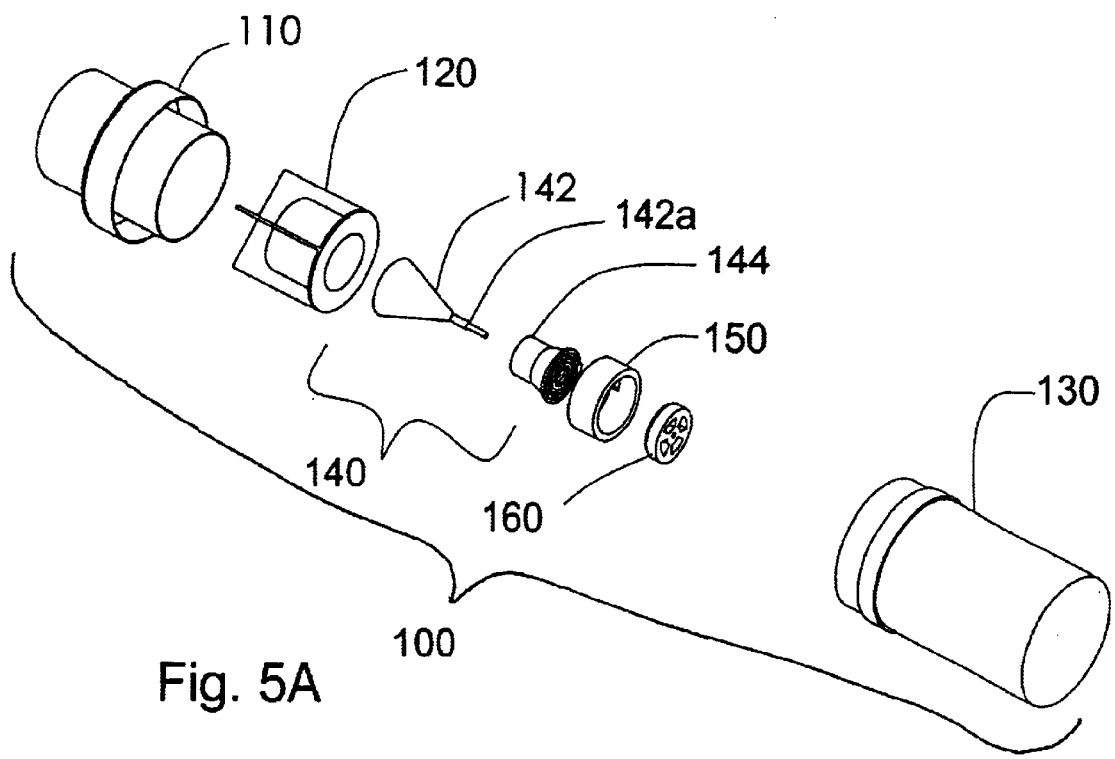
FIG. 5A illustrates an exploded or disassembled, perspective view of another embodiment of a sensor of the present invention in a closed state.
Figure 5B:
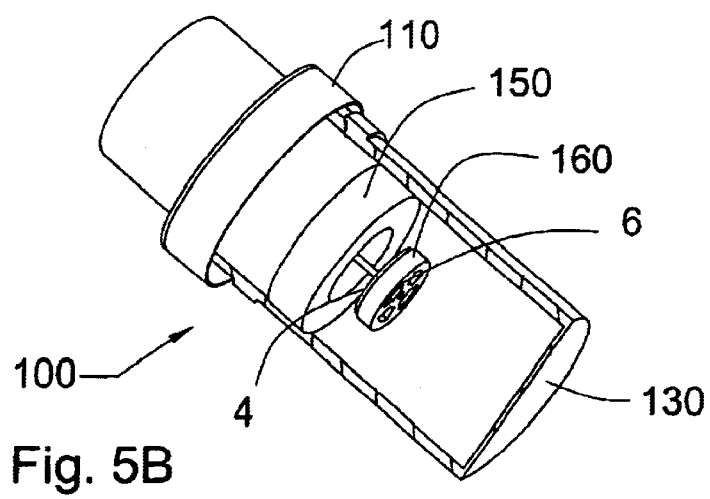
FIG. 5B illustrates a perspective view of the sensor of FIG. 5A in an assembled state, wherein the polymer disks are illustrated as transparent.

FIGS. 5A and 5B illustrate another embodiment of a sensor 100 of the present invention that operates in a manner similar to sensor 10. Sensor 100 includes an outer cup, container or cap 110, into which an inner container or reservoir 120 for a carrier fluid is positioned. As described above, the carrier fluid can be released to initiate one or more reactions. Cap 110 cooperates with a lower housing portion 130 (via, for example, threading) to enclose the components of sensor 110. Lower housing portion 130 thereby operates to protect the operating components of sensor 100 and is removed before activation of sensor 100 as described above.

In one embodiment, the reaction scheme of sensor 100 is an enzymatic equilibrium reaction scheme as described above in connection with sensor 10 in which a water carrier or vehicle provides both required moisture and enzyme substrate mobility by washing/mobilizing substrates from substrate-containing polymer disk 4 to an enzyme-containing polymer disk 6. To more clearly illustrate the other components of sensor 100, polymer disks 4 and 6 are not shown in FIG. 5A. Polymer disk 4 and polymer disk 6 are maintained in spaced separation by a separator or spacer 160. In an enzymatic biosensor for the detection of, for example, a toxic organophosphate, substrate-containing polymer disk 4 can be a polyurethane disk with butyrylcholine, urea and indoxyl acetate substrates, which diffuse out of substrate-containing polymer disk 6 when a release valve 140 (or other release mechanism) is engaged to release carrier water contained in reservoir 120.

Annular member or ring 150 preferably assists in retaining a release valve 140 in operative connection with reservoir 120. Annular member 150 can for example lock onto a lower flange of reservoir 120 via a threaded or bayonet connection as known in the art. In one embodiment a 20 mm release valve available from Waldwick Plastics of Waldwick, N.J. was used as release valve 140. Release valve 140 includes a seating 144 within which a spring loaded valve 142 is seated. A forward projection 142a of valve 142 projects forward through annular member 150 and through a passage formed in spacer 160. As described above, release valve 140 or other release mechanism (for example, an openable membrane) ensures that the carrier water (or other fluid carrier) remains within reservoir 120 until released on demand by firmly pressing enzyme-containing polymer disk 6 (see FIG. 5B) against a surface to be tested, thereby forcing projection 142a rearward and releasing carrier fluid via release valve 140.

The sensors of the present invention are particularly useful in the detection of toxic or hazardous substances such as nerve agents. The sensors of the present invention provide a number of substantial advantages over currently available nerve agent-sensing technologies including, but not limited to, simple use protocols, environmental compatibility, intuitive responses, increased safety and resistance to common interferants. Sensors 10 and 100 are entirely self-contained and simply pressed against a surface to initiate a reaction equilibrium between two enzymes. The substrate and enzymes are also each directly integrated within polymer layers to remove any requirement for applying additional substrates or extended incubation times, as is the case with conventional technologies.

The enzyme polymerization techniques used in the sensors of the present invention substantially stabilize incorporated enzymes, making sensors 10 and 100 resistant to many forms of interference that are problematic for currently available nerve agent sensing technologies. Such resistance results, for example, from the formation of multiple covalent bonds between the enzymes and the surrounding polymer matrix. The polymer essentially forms a protective barrier around the entrained enzymes, reducing the impact of environmental factors such as pH, temperature, and denaturants on enzyme performance. Table 1 illustrates the effect of certain types of interferants on sensor performance. Interferants of a chemical nature were added as a 10% solution to control and contaminated surfaces. It is clear that polymerization of the enzymes reduces the likelihood of false positive responses as well as masked signals due to interference.

TABLE 1

Effect of potential interference sources on sensor performance.

|  | M8 | M9 | M256 | M272 | CAM | Present Sensor |
|---|---|---|---|---|---|---|
| INTERFERENCE |  |  |  |  |  |  |
| High Temperature | Yes | Yes | Yes | Yes | No | No |
| Cleaning solvents | Yes | Yes | No | No | No | No |
| Petroleum products | Yes | Yes | Yes | Yes | Yes | No |
| Antifreeze | No | Yes | No | No | No | No |
| Insect repellant | Yes | Yes | Yes | No | Yes | No |
| Bleach | Yes | Yes | Yes | Yes | No | No |
| Water | No | Yes | No | No | No | No |

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A sensor for detecting an analyte in an environment, the sensor comprising:

a first reaction system including a first enzyme and a substrate for the first enzyme, the analyte inhibiting the first enzyme and at least a second reaction system including at least a first reagent and a second reagent that interact to produce a first detectable state when the first enzyme is inhibited; the first enzyme and the substrate being separated within the sensor, the first reagent and the second reagent being separated within the sensor; the sensor further including a reservoir containing a carrier fluid and an activator to release the carrier when the sensor it brought into contact with an environment to be tested for presence of the analyte, the carrier being suitable to mobilize the substrate for the first enzyme to contact the first enzyme and to mobilize the first reagent to contact the second reagent.

2. The sensor of claim 1 wherein the reaction of the first reaction system produces a second detectible state, different from the first detectible state.

3. The sensor of claim 1 wherein the reaction of the first reaction system causes pH to change in a first direction and the reaction of the second reaction system causes pH to change in a second direction, opposite of the first direction.

4. The sensor of claim 3 wherein the first enzyme is a hydrolase.

5. The sensor of claim 3 wherein the second reaction system comprises a second enzyme and a substrate for the second enzyme.

6. The sensor of claim 5 wherein the first enzyme is a hydrolase and the second enzyme is a different hydrolase.

7. The sensor of claim 3 wherein the first detectible is a colorimetric change.

8. The sensor of claim 3 wherein the reaction of the first reaction system produces a second detectible state, different from the first detectible state.

9. The sensor of claim 8 wherein the first detectible state arises from the presence of a first pH sensitive dye producing a colorimetric change and the second detectible state is a colorimetric change different from the colorimetric change of the first detectible state.

10. The sensor of claim 3 wherein the first enzyme is a cholinesterase.

11. The sensor of claim 10 wherein the analyte is a nerve agent.

12. The sensor of claim 1 wherein the reaction of the first reaction system causes a first colorimetric change and the reaction of the second reaction system causes a second colorimetric change, the second colorimetric change being different from the first colorimetric change.

13. The sensor of claim 12 wherein the first enzyme is a hydrolase.

14. The sensor of claim 12 wherein the second reaction system includes a second enzyme and a substrate for the second enzyme.

15. The sensor of claim 14 wherein the first enzyme is a hydrolase and the second enzyme is a different hydrolase.

16. The sensor of claim 12 wherein the first enzyme is a cholinesterase.

17. The sensor of claim 16 wherein the analyte is a nerve agent.

18. The sensor of claim 1 wherein the reaction of the first reaction system causes pH to change in a first direction and the reaction of the second reaction system causes a pH sensitive colorimetric change when the first enzyme is inhibited.

19. The sensor of claim 18 wherein the first enzyme is a hydrolase.

20. The sensor of claim 18 wherein the second reaction system includes a second enzyme and a substrate for the second enzyme.

21. The sensor of claim 20 wherein the first enzyme is a hydrolase and the second enzyme is a different hydrolase.

22. The sensor of claim 18 wherein the first enzyme is a cholinesterase.

23. The sensor of claim 22 wherein the analyte is a nerve agent.

24. The sensor of claim 1 wherein the first enzyme is immobilized in a polymer medium.

25. The sensor of claim 1 wherein the first enzyme is immobilized in a first polymer medium, the second reagent of the second reaction system is a second enzyme that is immobilized in the first polymer medium.

26. The sensor of claim 25 wherein the substrate for the first enzyme is incorporated within a second polymer medium and the first reagent of the second reaction system is a substrate for the second enzyme and is also incorporated within the second polymer medium.

27. The sensor of claim 25 wherein the activator releases the carrier fluid when the first polymer medium is contacted with a surface to be tested for presence of the analyte.

28. The sensor of claim 27 further including a removable transparent housing member to enclose the sensor.

29. The sensor of claim 28 further including a barrier to prevent contact between the first polymer medium and the second polymer medium.

30. A sensor for the detection of an analyte, comprising:
a first reagent in one section of a housing;
at least a second reagent in another section of the housing, wherein said second reagent is separated from said first reagent in said housing, and wherein said second reagent is immobilized in a first polymer medium and wherein said first reagent is incorporated in a second polymer medium;
a reservoir of a carrier fluid within the housing;
a release mechanism in operable connection with the reservoir that is activated to release said carrier fluid when the sensor is brought into contact with an environment to be tested for the presence of the analyte, the carrier fluid mobilizing the second reagent to contact the first reagent with the second reagent, the interaction of the first reagent and the second reagent being affected by the presence or absence of the analyte to cause a measurable change in state within the sensor.

31. The sensor of claim 30 further including:
a third reagent in one section of the housing;
at least a fourth reagent in another section of the housing;
the carrier fluid mobilizing the third reagent to contact the third reagent with the fourth reagent, the interaction of the third reagent and the fourth reagent being affected by the presence or absence of the analyte to cause a measurable change of state within the sensor.

32. The sensor of claim 31 wherein the second reagent is immobilized in the first polymer medium and the fourth reagent is immobilized in the first polymer medium.

33. The sensor of claim 32 wherein the first reagent and the third reagent are incorporated within the second polymer medium.

34. A sensor for the detection of an analyte, comprising:
a first reagent in one section of a housing;
at least a second reagent in another section of the housing;
a reservoir of a carrier fluid within the housing;
a release mechanism in operable connection with the reservoir that when activated causes carrier fluid to be released from the reservoir, the carrier fluid mobilizing the second reagent to contact the first reagent with the second reagent, the interaction of the first reagent and the second reagent being affected by the presence or absence of the analyte to cause a measurable change of state within the sensor;
a third reagent in one section of the housing;
at least a fourth reagent in another section of the housing, wherein the carrier fluid mobilizing the third reagent to contact the third reagent with the fourth reagent, the interaction of the third reagent and the fourth reagent being affected by the presence or the absence of the analyte to cause a measurable change of state within the sensor, wherein the second reagent is immobilized in a first polymer medium and the fourth reagent is immobilized in the first polymer medium, and wherein the first reagent and the third reagent are incorporated within a second polymer medium; and wherein an activator releases the carrier fluid when the first polymer medium is contacted with a surface to be tested for presence of the analyte.

35. The sensor of claim 34 further including a removable transparent housing member to enclose the sensor.

36. The sensor of claim 35 further including a barrier to prevent contact between the first polymer medium and the second polymer medium.

* * * * *